United States Patent [19]

Hsu et al.

[11] Patent Number: 4,712,865
[45] Date of Patent: Dec. 15, 1987

[54] DYE CONTAINING SILICON POLYMER COMPOSITION

[75] Inventors: Li-chien Hsu, Mission Viejo; Hal Heitzmann, Irvine, both of Calif.

[73] Assignee: Baxter Travenol Laboratories, Deerfield, Ill.

[21] Appl. No.: 529

[22] Filed: Jan. 5, 1987

[51] Int. Cl.⁴ .......................... C07F 7/08; C07F 7/10; C07F 7/12
[52] U.S. Cl. .................... 350/96.29; 528/43; 528/34; 8/523; 8/581; 8/632; 8/648; 128/634
[58] Field of Search .................. 8/523, 632, 581; 556/419; 528/43, 34; 128/634

[56] References Cited

U.S. PATENT DOCUMENTS

| | | | |
|---|---|---|---|
| 4,506,058 | 3/1985 | Ashby | 524/730 |
| 4,560,679 | 12/1985 | Toyoshima | 514/63 |
| 4,613,667 | 9/1986 | Marraccini | 546/14 |

*Primary Examiner*—A. Lionel Clingman
*Assistant Examiner*—Isabelle Rodriguez
*Attorney, Agent, or Firm*—Perman & Green

[57] ABSTRACT

A preparation of dye-containing gas permeable silicon polymer and resin compositions are disclosed. Homopolymers and/or co-polymers of polysiloxane are formed in which a photoactive center substituent containing a dye is covalently bonded to the matrix structure thereby rendering the dye non-diffusible. These dye-silicone polymer compositions have particular utility in gas sensing fiber optics devices.

5 Claims, No Drawings

DYE CONTAINING SILICON POLYMER COMPOSITION

BACKGROUND OF THE INVENTION

The present invention relates to the preparation of photoactive dye containing silicone polymer compositions. In particular, the present invention is directed to a specific dye-silicone polymer composition in which the dye is present in non-diffusible form thereby rendering the dye containing silicon polymers particularly useful for certain biochemical applications.

The development of glass or plastic fibers, a fraction of a millimeter in diameter, for in vivo biomedical measurements, is a relatively new and important endeavor. Fiber-optic sensors can be as small as electrosensors and offer several distinct advantages. They are safe, involving no electrical connection to the body; the optical leads, very small and flexible, can be included in catheters for multiple sensing; and materials suitable for long term body implantation such as plastic, may be used.

The mechanism of fiber-optic sensor operation is relatively simple. Light from a suitable source travels along an optically conducting fiber to a receptor terminal where reflection, scattering or luminescence occurs. The affected light is then returned to a light measurement instrument which interprets the returned signal. The light emanating from the sensing end of the fiber may be reflected by a tiny transducer that varies the reflectance with some parameter of interest, the light may be back scattered by the medium into which the fiber is inserted, or the returned light may be engendered from luminescence of something at the end of the fiber that was energized by the illuminating light. Of these three general types of in-vivo fiber-optic sensing mechanisms, the luminescence technique has been recently developed as a measurement to determine the amounts of physiological gasses in blood.

The presence of unusually high or low oxygen content in blood samples may indicate various abnormalities. Peterson et al in U.S. Pat. No. 4,476,870 developed an optical sensor for measuring physiological oxygen gas, $PO_2$. The device is based on the quenching of the fluorescence of certain dyes by oxygen gas. Dyes are chosen for visible light excitation and are distributed on an adsorptive support medium for use as the light scattered terminal for the ingress and egress optical fiber waves. Generally, an inorganic absorbant, such as silica gel, is used in the dye support medium. However, it has been found that such adsorbant materials are humidity-sensitive, thereby seriously interfering with fluorescence at high humidity. The $PO_2$ optical fiber probe is similar to other gas sensors and reproduces the basic concept of utilizing an indicator packing in a gas permeable container at the end of a pair of optical-fibers.

While the $PO_2$ probes of Peterson are effective the sensor suffers two disadvantages. First the indicator is a two piece structure comprising a microporous gas permeable envelope which houses a porous packing on which an oxygen quenching dye is adsorbed. As developed by Peterson, these dyes are adsorbed on an organic or inorganic medium and encapsulated in a microporus gas permeable polypropylene envelope. The two part indicator system renders manufacturing more difficult and adsorbants must be carefully selected. As indicated above, inorganic silica adsorbants are ineffective because of their humidity sensitivity. It has also been found that organic adsorbants, such as polystyrene, are deficient in that the dyes from the probe leach out into the blood stream, thereby losing their effectiveness as well as their reusability.

Because of the importance of fiber-optic $PO_2$ sensors, a need exists to develop or find a unitary indicator comprising a solid gas permeable carrier material which can act as a support medium for the fluorescent dye so that leaching of the dye does not occur during use and the sensor can be used and reused effectively and dependably under any environmental conditions. It is well known that silicone polymers are gas permeable materials having been used in artificial lungs. It has now been found that chemically attaching dyes on certain polysiloxane polymers provides an optimum non diffusible dye indicator system for use in fiber-optic sensors.

OBJECTS OF THE INVENTION

It is therefore an object of this invention to provide novel fluorescent dye containing polysiloxanes.

It is a further object of this invention to provide a method for preparing novel polynuclear aromatic hydrocarbon dye containing polysiloxane polymers by reacting a polysiloxane with particular polynuclear aromatic compounds in the presence of certain organo functional/silicone functional silane coupling agents.

It is still a further object of this invention to provide polymeric fluorescent compositions for use in fiber-optic biological sensor devices.

It is yet a further object of the present invention to provide a novel oxygen quenching sensor for use in a $PO_2$ fiber-optic probe.

SUMMARY OF THE INVENTION

In accordance with the present invention, there is provided a fluorescent polymer composition having gas permeability characteristics and high oxygen quenching capability, wherein the composition is comprised of a polysiloxane backbone structure having a polynuclear aromatic hydrocarbon based fluorescent dye chemically attached thereto. The novel dye containing polysiloxanes are prepared by utilizing a unique organo-functional/silicone functional silane coupling agent to cause the chemical linkage between the polynuclear aromatic hydrocarbon dye and the polysiloxane.

The dye containing polysiloxanes of the present invention exhibit high gas permeability and acute oxygen quenching fluorescence which make them a desirable unitary indicator system for optical sensors for measuring physiological oxygen gas. As will hereinafter be illustrated, the dye containing polysiloxane compositions of the present invention may be directly employed as the unitary sensor element at the terminal of optical wires to indicate oxygen gas changes in blood. Due to the high gas permeability of silicone polymers and a covalent linkage of the dye molecules to the polymer, optical probes made with the instant composition are non-dye diffusible and completely reusable.

DETAILED DESCRIPTION OF THE INVENTION

The fluorescent dye containing polysiloxane polymers of the present invention comprise homopolymers or copolymers of polysiloxane linear polysiloxanes of the formula:

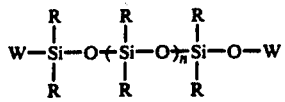

and branched polysiloxanes having at least one branch point on the backbone chain and corresponding to the general formula:

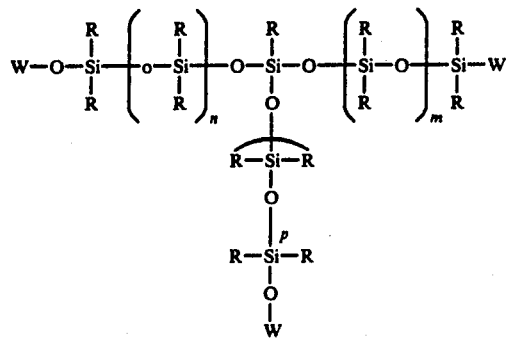

Wherein n, m and p are independently integers of 1 to 10,000; the R groups are independently hydrogen hydroxyl, halogen or alkyl, aryl, alkenyl, acyloxy, and alkoxy groups of up to 30 carbon atoms or the photoactive center and independently substituated W having the following formula:

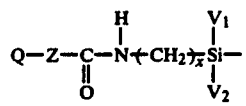

Where Q is a polynuclear aromatic hydrocarbon based fluorescent dye; x is an integer of from 1 to 10; Z is a hydrocarbon of up to 50 carbon atoms; and $V_1$ and $V_2$ are independently any hydrocarbon of up to 50 carbon atoms or a hydrogen, halogen, hydroxyl, alkoxy, acyloxy or alkenyl group. It is to be understood that one of the R group substituents is the photoactive center group W.

While any and all polynuclear aromatic hydrocarbon based fluorescent dye Q substituents are applicable to the present invention, preferred dyes are fluorescent polynuclear aromatics selected from the group of pyrene, perylene, benzoperylene and derivatives thereof having the following structural formula:

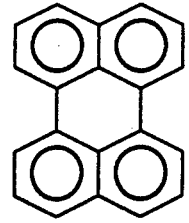

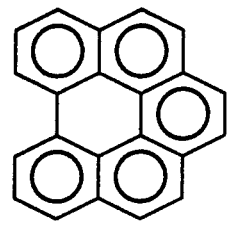

As indicated the R groups may independently be the substituents recited above, preferred substituents include methyl phenol, vinyl, fluoralkyl and hydrogen.

The fluorescent polysiloxane polymers of the present invention can be conveniently prepared by reacting an active site substituted branched or linear polysiloxane co-polymer or homopolymer and an isocyanate reactive end group substituted polynuclear aromatic fluorescent dye in the presence of organo functional/silicone functional silane coupling agents having the formula:

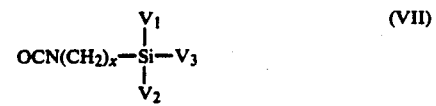

where x, $V_1$ and $V_2$, are the same as defined above and $V_3$ is the same as $V_1$ and $V_2$ with the proviso that at least one of the $V_1$, $V_2$ or $V_3$ substituents be silicone polymer reactive groups of hydrogen, halogen, alkenyl, acyloxy, alkoxy, amine or amide. The isocyanate group of the coupling agent is reactive with the substituted isocyanate reactive end group of the fluorescent dye while at least one of the $V_1$, $V_2$ or $V_3$ substituents is reactive with an active site substituted on the polysiloxane. An alternative means of preparing the instant compositions involves reacting the isocyanate reactive end groups substituted dye with the coupling agent to form a dye/silicone functional silane adduct of co-pending application Ser. No. 000,537. The adduct is subsequently reacted with an active site substituted polysiloxane prepolymer to yield a fluorescent dye containing polysiloxane as illustrated in formulas I and II.

By any active site substituted polysiloxanes is meant those substituents of polysiloxanes that will react with the silicone functional $V_1$, $V_2$ and $V_3$ groups of the silane coupling agent. Examples of such active site substituents include hydroxyl, alkoxyl, acyloxyl and amine groups.

An exemplary preparation of the instant polymeric dyes involves reacting a silanol terminated linear polydimethylsiloxane ("PDMS") having the formula:

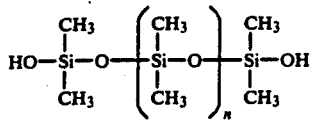

where n is the same as defined above, with an alkyl hydroxyl substituted polynuclear aromatic fluorescent compound such as pyrene butanol having the following formula:

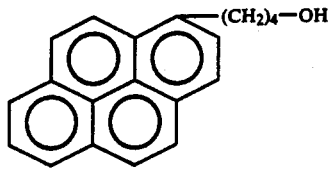

in the presence of 3-isocyanato-propyl dimethyl chlorosilane coupling agent having the formula:

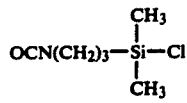

The reaction yields a pyrene terminated linear polysiloxane conforming to formula I. Alternatively, the pyrene butanol and the chlorosilane coupling agent could have been reacted together to form an adduct and the adduct subsequently reacted with the PDMS.

While the pyrene, perylene and benzoperylene polynuclear aromatic hydrocarbon fluorescent dyes of the present invention as represented in formulas IV, V and VI are preferred materials, any dyes may be used within the spirit and scope of the present invention. As indicated the dye reactant should be substituted with an isocyanate reactive group to ensure reaction with the isocyanate portion of the coupling agent. Illustrative polynuclear dye reactants include the butanol derivatives of pyrene, perylene and benzoperylene family of dyes. However, inasmuch as the isocyanate group of the coupling agent reacts with the hydroxyl group on butanol chain any functional group which is reactive with the isocyanate can be used as a reactant on the polynuclear aromatic hydrocarbon fluorescent dye. Therefore carboxylic acid, amine, amides and other groups could be reactive substituents on the fluorescent dye. For example, pryrene butanoic acid would be an effective reactant within the purview of the present invention. This point is more amply demonstrated in co-pending application Ser. No. 000,537 to Silane Dye Compositions.

The method of the present invention is performed by techniques typically used with polysiloxane polymers. In one embodiment more fully outlined in the copending application referred to above, an aliphatic alcohol-substituted polynuclear aromatic fluorescent dye is dissolved along with an organo functional/silicone functional silane coupling agent and a tin octoate catalyst in an appropriate solvent. Thereafter, the resulting dye-silane adduct is added to a hydroxyl-terminated polysiloxane. The coupling reaction takes place and the fluorescent dye-terminated polysiloxane is recovered. Catalysts well known to those skilled in silicone chemistry may be used typical ones being tin octoate, zinc octoate, and dibutyl tin dilaurate.

The fluorescent-dye substituted polysiloxane homopolymers and co-polymers produced according to the present invention are both linear and branched chain polysiloxanes having varying molecular weights and a plurality of repeating units having the formulas as listed above. The polymer will be substituted by the fluorescent dye groups present in the particular aliphatic functionally substituted polynuclear aromatic dye. This is clearly demonstrated in formula II above where the photoactive side group W can be covalently linked to any part of the resin structure.

The polymer dyes of this invention are useful in a variety of applications for which dyes are conventionally employed. However, as discussed above, a particularly preferred and desired use for these polymeric dyes is in the indicator portion of fiber-optic chemical sensors, especially fiber-optic $PO_2$ probes as described in U.S. Pat. No. 4,476,870 to Peterson. These polymeric dyes are particularly attractive for use in such probes because the polynuclear aromatic hydrocarbon based fluorescent dyes used within the purview of the present invention are oxygen quenching and their chemical linkage to the polysiloxane molecular render the dye non diffusable and prevents any desorption when placed in contact with a blood medium.

The amount of polynuclear aromatic fluorescent dye incorporated into the polysiloxane molecule can vary depending upon the amount of active site functional groups in the polysiloxane starting material and the reaction conditions.

The following examples are included for further understanding of the invention. It should be understood that these examples are in no way intended to limit the scope of the present invention.

EXAMPLE I

The following example illustrates the preparation of a dye/silane adduct starting material of copending application Ser. No. 000,537 used in the preparation of the present dye containing polysiloxanes. The mole ratio of pyrene butanol to isocyantopropylchlorosilane was 1 to 20. Tin Octoate was used as the catalyst at a 0.1% level (weight of catalyst to the weight of reactants).

Pyrene butanol was dissolved in methylene chloride (about 0.4% w/v). The catalyst, tin octoate, was then added, while stirring. Minor amounts of isocyantopropylchlorosilane at small increments were added to the solution over a period of 30 minutes. A significant increase in molecular weight was observed after the mixture was agitated at room temperature for one hour. A Gel Permeation Chromatographic Analysis (GPC) demonstrated the molecular weight increase which indicated that a dye containing molecule had been formed.

EXAMPLE II

The following experiment demonstrates the direct preparation of a pyrene dye terminated polydimethyl siloxane. The mole ratio of pyrene butanol to isocyantopropylchlorosilane and polydimethylsiloxane silanol (Formula Weight 3200, viscosity-80 CTS) was 1:10:20. Tin Octoate was used as the catalyst at 0.01% level.

Pyrene butanol (0.4/100 V/W) was dissolved in methylene chloride. Stirring occurred and Tin Octoate was added. Small amounts of isocyantopropylchlorosilane and polydimethylsiloxane silanol were added dropwise over a period of 30 minutes. After all components were added to the solution, the mixture was agitated continuously for two hours at room temperature. A GPC analysis demonstrated a new compound of increased molecular weight indicating that the pyrene butanol chemically linked to the polysiloxane by means of reaction with the organo functional/silicone functional silane coupling agent, isocyantopropylchlorosilane, thereby forming pyrene containing polydimethyl siloxane.

EXAMPLE III

The following illustrates the use of the dye terminated adduct of Example I in a one part in room temperature vulcanizable silicone systems and the preparation of an optical sensor device.

The fluorescent dye/silane adduct prepared in Example I is blended into a one part moisture cured silicone elastomer sealant containing acetoxy terminated polydimethylsiloxane. When the blend was cured it was found that the dye/silane adduct had been chemically immobilized into the crosslinked elastomeric structure. Before the blend was cured a fiber optical probe was dipped into the blend and allowed to cure thereby forming a gas permeable solid integral indicator terminal (Probe 1).

EXAMPLE IV

The following illustrates the use of the dye-isocyanosilane adduct of Example I in a two part room temperature vulcanizable silicone system.

The dye/isocyano silane adduct prepared in Example I is blended into a two part room temperature vulcanizable elastomer comprising silanol terminated polydimethylsiloxane as the matrix backbone, triethoxysilane as the crosslinker and tin octoate as the catalyst. Upon curing there results a product which has the desired physical properties of being clear and tack free. An indicator terminal for an optically active fiber was prepared (Probe 2) in the same manner as Example III.

EXAMPLE V

As a control, a blend of pure pyrene dye and the one part moisture cured silicone elastomer was prepared as in example I.

An indicator terminal for an optically active fiber was prepared (Probe 3) in the same manner as Example III.

The optical probes prepared in Examples III, IV and IV were then subjected to leachability tests to determine dye retentivity during blood flow conditions. Bovine blood loops with a bubbler oxygenator were set up for sensor evaluation. The blood flow rate was 4 LPM, and 6% $CO_2$ balanced air was run at 2 LPM. Each sensor tip was sequentially exposed to pure Nitrogen (baseline), Oxygen and Air and to establish the sensitivity of the dye/silicone polymer indicator to oxygen quenching. After exposure, the sensor was placed against the blood flow for a period of two to four hours. The fluorescence signal was monitored via a Perkin Elmer LS-5 Fluorometer with beam splitter set at an exitation wavelength of 346 nm with a UG II filter and emission wavelength at 400 nm. The results of this test for each probe are listed as follows in Table I.

TABLE I

| | Before Leaching | After 4 hrs. Leaching |
| --- | --- | --- |
| PROBE 1 | | |

TABLE I-continued

| | Before Leaching | After 4 hrs. Leaching |
| --- | --- | --- |
| (Example III) | | |
| $N_2$ | 289 | 310 |
| Air | 179 | 178 |
| $O_2$ | 118 | 119 |
| PROBE 2 | | |
| (Example IV) | | |
| $N_2$ | 179 | 180 |
| Air | 118 | 118 |
| $O_2$ | 81 | 81 |
| PROBE 3 | | |
| (Example V) | | |
| $N_2$ | 258 | 198 |
| Air | 232 | 197 |
| $O_2$ | 220 | 196 |

As can be appreciated from the data, there is virtually no loss of signal after leaching in Probes 1 and 2 thereby validating the effect of chemically bonding the fluorescent dye to the silicone elastomers. However, there is almost complete diffusion of the dye after leaching in probe 3 which demonstrates that admixing pyrene in a silicone elastomeric blend is ineffective in obtaining a non-diffusible probe indicator.

Although variations are shown in the present application, many modifications and ramifications will occur to those skilled in the art upon a reading of the present disclosure. These, too, are intended to be included herein.

What is claimed:

1. A dye containing solid gas permeable silicone composition comprising a polysiloxane polymer structure and a polynuclear aromatic hydrocarbon/silane photoactive center substituent chemically attached to the polymer structure, wherein the dye containing polysiloxane polymer is a linear siloxane having the formula

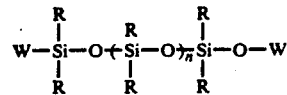

wherein n is an integer of from 1 to 10,000; R is independently selected from hydrogen, hydroxyl and halogen or alkyl, aryl, alkenyl, acyloxy and alkoxy groups of up to 30 carbon atoms or the silane photactive center substituent, W having the following formula:

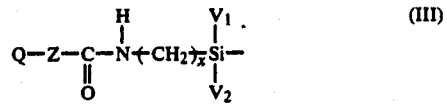

where Q is a polynuclear aromatic hydrocarbon based fluorescent dye; x is an integer of from 1 to 10; Z is a hydrocarbon of up to 50 carbon atoms and $V_1$ and $V_2$ are independently any hydrocarbon of up to 50 carbon atoms or hydrogen, halogen, aryl, hydroxyl, alkoxy, acyloxy or alkenyl substituent.

2. The linear polysiloxane of claim 1 wherein the polynuclear aromatic hydrocarbon based fluorescent dye Q is selected from the group consisting essentially of pyrene, perylene, benzoperylene and derivatives thereof.

3. The composition of claim 1 wherein $R_1$ is selected from the group consisting essentially of methyl, hydrogen, phenol, vinyl, and fluoroalkyl substituents.

4. The composition of claim 1 wherein the dye containing polysiloxane polymer structure is a branched siloxane having the following formula:

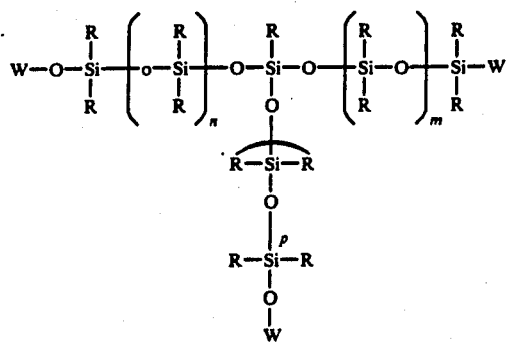

Wherein n, m and P are independently integers of 1 to 10,000; The R groups are independently hydrogen, hydroxyl, halogen or alkyl, aryl, alkenyl, acyloxy, and alkoxy groups of up to 30 carbon atoms or the photoactive center side group substituent W having the following formula:

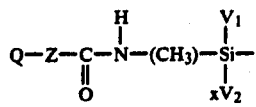

where Q is a polynuclear aromatic hydrocarbon based fluorescent dye; x is an integer of from 1 to 10; Z is a hydrocarbon of up to 50 carbon atoms; and $V_1$ and $V_2$ are independently any hydrocarbon of up to 50 carbon atoms or hydrogen, halogen, aryl, hydroxyl, alkoxy, acyloxy, or alkenyl substituent.

5. An optical probe comprising:
  (a) at least one fiber optic wire strand; and
  (b) an integral indicator terminal for the fiber optic wire comprising a dye containing solid gas permeable silicone composition comprising a polysiloxane polymer structure and a polynuclear aromatic hydrocarbon based fluorescent dye chemically attached to the polymer structure.

* * * * *